United States Patent [19]

Renz

[11] Patent Number: 5,053,326

[45] Date of Patent: Oct. 1, 1991

[54] HYBRIDIZATION METHOD AND PROBE

[75] Inventor: Manfred Renz, Heidelberg, Fed. Rep. of Germany

[73] Assignee: Europaisches Laboratorium fur Molekularbiologie (EMBL), Heidelberg, Fed. Rep. of Germany

[21] Appl. No.: 724,307

[22] Filed: Apr. 17, 1989

Related U.S. Application Data

[63] Continuation-in-part of Ser. No. 684,644, Nov. 16, 1984, abandoned.

[30] Foreign Application Priority Data

Mar. 22, 1983 [DE] Fed. Rep. of Germany ....... 3310337

[51] Int. Cl.$^5$ .................. C12Q 1/68; G01N 33/566; A61K 37/08; C07K 3/00
[52] U.S. Cl. ........................ 435/6; 435/803; 435/810; 436/501; 530/358; 530/395; 935/78
[58] Field of Search ............... 435/6, 810, 803; 436/501; 935/78; 530/358, 395

[56] References Cited

U.S. PATENT DOCUMENTS

| 4,152,411 | 5/1979 | Schall, Jr. .................. 436/800 X |
| 4,302,204 | 11/1981 | Wahl et al. .................. 435/805 X |
| 4,556,643 | 12/1985 | Paau et al. .................. 435/6 X |
| 4,581,333 | 4/1986 | Kourilsky et al. .................. 435/6 |

OTHER PUBLICATIONS van Eekelen, C. et al., *Nucleic Acids Research*, vol. 10, No. 10, 1982, pp. 3039-3052.
Manning, J. et al., *Biochemistry*, vol. 16, No. 7, 1977, pp. 1364-1370.
Renz, M. et al., *Nucleic Acids Research*, vol. 12, No. 8, 1984, pp. 3435-3444.
Meinkoth, J. et al., *Anal. Biochem.*, vol. 2, No. 2, 1984, pp. 267-269.
Alberts, B. et al., Molecular Biology of the Cell, Garland Pub. Inc., N.Y., 1983, p. 389.
Kennell, D. E., In: Progress in Nucleic Acid Research and Molecular Biology (Davison, J. N. et al., ed.), vol. 11, 1971, Academic Press, N.Y., pp. 259-261.

*Primary Examiner*—Jacqueline Stone
*Assistant Examiner*—David T. Fox
*Attorney, Agent, or Firm*—Wenderoth, Lind & Ponack

[57] ABSTRACT

In order to carry out hybridization reactions by forming a complex between a polynucleotide and a detectable substance and using the complex thus formed for hybridization reactions, a single strand polynucleotide is reacted with a positively charged nucleic acid binding detectable protein or polyamine in solution and the resultant complex is covalently bound with a cross-linking agent and the polynucleotide compound obtained is used as a marker in hybridization experiments in the elucidation of complementary sequences in foreign polynucleotides. The protein may be an enzyme such as horseradish peroxidase modified by a polyamine e.g. a polyethylene imine to provide a positively charged region. Assay sensitivity may be enhanced by performing the hybridization in the presence of about 6% (w/v) of a polyethylene glycol.

3 Claims, 2 Drawing Sheets

HYBRIDIZATION METHOD AND PROBE

This is a CIP of Ser. No. 684,644 filed 16th Nov. 1984 now abandoned which is the U.S. National Phase of PCT/DE84/00051, filed Mar. 9, 1984.

The invention relates to methods for detecting target nucleotide sequences in polynucleotide material by hybridization techniques and probes suitable for use in the methods.

Hybridization is a means of determining the identity of nucleotide sequences in two different polynucleotide chains. Two DNA chains with complementary nucleotide sequences form a doublestrand structure with one another on cooling in defined conditions. Numerous problems in molecular biology, for example the location and isolation of specific genes or gene fragments, the mapping of gene sequences and the like, can thus be solved by hybridization. The location of specific sought-after genes plays a decisive role particularly in gene technology, and hybridization makes such a location possible.

In order to carry out the hybridization reaction a nucleotide sequence having a structure complementary to that of the target sequence is used, and is suitably labelled for the redetection. This labelling was previously normally performed by enzymatic introduction of radioisotope-bearing nucleoside triphosphates into the complementary polynucleotide used for the identification. A considerable disadvantage of this method is the need to use radioactive substances, which requires comprehensive safety measures as well as expensive apparatus and equipment.

Attempts have therefore already been made to replace radioactive labelling by other forms of labelling.

Thus, nucleotide analogues have recently been synthesised, which contain biotin covalently bonded to a pyrimidine or purine ring. These nucleotide derivatives are substrates for RNA and DNA polymerases and polynucleotides formed under the action of these enzymes hybridize specifically with their complementary sequences. In conjunction with an affinity detection system (e.g. avidin peroxidase) or an immunological detection system (e.g. biotin antibodies in combination with a second peroxidase-carrying antibody), these probes can be used as an alternative to radioactively labelled nucleic acids. Biotin residues have also already been coupled with RNA via cytochrome C and the hybridizations have been located by electron microscopy using the avidin detection system (Chromosoma/-Berl. 53, 107–117 [1975]).

This process is however still relatively complex since it requires several synthesis steps. There is still a need therefore for a simpler hybridization method and a hybridization reagent which is suitable as a probe and is simple to prepare, and which improves the sensitivity of the hybridization techniques.

The object of the invention is thus to provide such methods and probes.

In one aspect the invention provides a method of detecting a target nucleotide sequence in polynucleotide material by contacting the material under hybridizing conditions with a probe containing a nucleotide sequence complementary to the target sequence and thereafter using the probe to detect the target sequence in the material, characterized in that the probe comprises a complex of the complementary nucleotide sequence with a detectable positively charged nucleic acid binding protein or polyamine.

In another aspect the invention provides a probe suitable for use in hybridization reactions which comprises a complex of a single-stranded polynucleotide with a detectable positively charged nucleic acid binding protein or polyamine.

Within the scope of the invention, positively charged nucleic acid binding proteins or polyamines are understood to be those which either possess this property per se or, if they are negatively charged or are neutral, have been modified with a correspondingly positively charged protein or polyamine. It was also surprisingly found that any arbitrary protein can be converted into a DNA-binding protein by modifying it with a positively charged protein or polyamine.

The invention thus provides a simple process for preparing hybridization probes which enables even large protein molecules to be introduced as labelling substances. The process is based on the fact that a positively charged protein or polyamine binds by electrostatic interactions to a nucleic acid at low ionic strength, and thus promotes cross-linking reactions between nucleic acid and protein or polyamine. Single strand DNA and a lysine-rich, DNA-binding chromosomal protein, such as e.g. histone H1, may be used. The high lysine content of such proteins satisfies two requirments, viz.:

1. A very intimate binding to nucleic acids is achieved, which therefore enables a very effective cross-linking to take place with low concentrations of cross-linking agent such as e.g. glutaraldehyde with short reaction times. Protein-polynucleotide complexes (probes) prepared in this way are not single strand DNA labelled with protein, but constitute covalently bound single strand DNA-protein units with a protein : DNA mass ratio of nearly 1. After hybridization the complementary sequences can now be detected by searching for the protein (e.g. with an antibody).

2. Proteins or polyamines can easily be chemically modified. In the case of histone H1, modification takes place e.g. at the $\epsilon$-amino group of the lysine radical. In this connection, labelling groups or compounds can be fixed directly or via bridge-forming compounds such as e.g. cyclic N-succinimide esters, to the amino goup. Labelling of the lysine amino group has little effect on the nucleic acid binding property of the protein since not all lysine radicals are required for strong nucleic acid-protein interactions. By this method many histone H1 molecules (now labelled) can be cross-linked with single strand DNA, and markers with a large number of labelled sites can be obtained, which can easily be determined after hybridization with an affinity or immunological detection system. Blot hybridization experiments show that under identical reaction conditions, labelled probes corresponding to the method according to the invention react with a high degree of specificity with their complementary sequences and are indistinguishable from nick-translated or end-labelled probes.

Within the scope of the invention, in principle all positively charged polymers and oligomers of amino acids of natural or synthetic origin, such as for example poly-lysine, chromosomal proteins including histones, and single strand specific binding proteins such as e.g. gene-32 protein, are suitable as positively charged nucleic acid binding proteins. Polyamines are also suitable. Of the latter, the naturally occurring, so-called "polyamines" such as spermidine, spermine, putrescine and the like, which in some cases are actually oligoamines, are preferred. Synthetic polyamines are however also suitable.

According to a preferred feature of the invention, a detectable protein which is not itself positively charged can be modified by means of a positively charged protein or polyamine. This modification is widely applicable and enables any detectable protein to be brought into a form in which it can form a complex with nucleotide sequence. For example, enzymes such as horseradish peroxidase and alkaline phosphatase can be suitably modified.

The modifier may be a positively charged protein such as histone H1, but is preferably a polyamine. It does not appear necessary that the polyamine contains a large number of primary amino groups. For example, I have successfully used polyamideamine (PAA), polyethyleneimine (PEI) and polyaminepolyether (PAP), the last two being particularly satisfactory; but the numbers of primary amino groups are in the ratio PEI > PAA > PAP. The molecular weight of the polyamine does not appear to be critical, as for example PEI of molecular weight from 1400 to >120,000 have been used successfully. The amount of polyamine required is quite small, and from 0.05% to 10%, e.g. from 0.08% to 1.2%, by weight of the detectable protein is generally adequate to modify the protein in the desired manner.

Modification may be effected by bringing the detectable protein and the polyamine or other modifier together in an aqueous medium in the presence of a cross-linking agent. The cross-linking agent may have the property of reacting under specified conditions (e.g. low pH) with carbohydrate moieties associated with the protein, and under other conditions (e.g. raised pH) with primary or other amino groups. Suitable cross-linking agents will be known to those skilled in the art, and may include sodium periodate; N-succinimidyl-3-(2-pyridyldithio) propionate; ultraviolet light; and p-benzoquinone which is preferred. The cross-linking agent may be reacted with one reagent, e.g. the protein, prior to addition of the other under altered conditions.

The single strand polynucleotide may similarly be of natural or synthetic origin, and is preferably a DNA or RNA. DNA and RNA may also be used as hybridization reaction partners, with the result that the hybridization reaction itself can involve DNA with DNA, DNA with RNA and RNA with RNA.

The complex formed from single strand polynucleotide and the positively charged nucleic acid binding protein or polyamine (which term includes detectable protein modified with a positively charged protein or polyamine) is crossed-linked with conventional cross-linking agents which are capable of binding the functional groups of the protein to the functional groups of the polynucleotide. Particularly suitable are bifunctional cross-linking agents such as dialdehydes, for example glutaraldehyde, diepoxides and, in general, compounds bearing two suitable functional groups for alkylation in aqueous solution. Typical groups suitable for this purpose are activated carboxyl groups such as acid chlorides, acid bromides, acid anhydrides, halogen atoms activated by adjacent double bonds, and the like.

The solution for carrying out the complex formation reaction between the protein or polyamine and the single strand polynucletide should have a low ionic activity. The ionic strength should preferably be less than 50 mM.

In order to make the hybridization product visible, the protein contained therein must be made detectable, e.g. by labelling, or by virtue of its own activity e.g. if it is an enzyme.

The protein or polyamine can be labelled either before carrying out the complex formation reaction or can be carried out on the already formed and optionally also already cross-linked complex. Labelling is carried out according to the methods of protein chemistry known for this purpose, which are known to those skilled in the art and need not be described in more detail here. Both radioactive labelling and labelling with dyes, dye components or fluorescent or chemiluminescent materials, or biologically active proteins, such as e.g. enzymes, are suitable as labelling systems.

The hybridization reaction itself may be performed in accordance with the known methods of simply adding the covalently cross-linked complex obtained as described from the single strand polynucleotide and the positively charged nucleic acid binding protein or polyamine, to a solution containing the complementary target nucleotide sequence acid, and incubating, preferably at a somewhat elevated temperature. Alternatively, the polynucleotide material including the target sequence may be immobilised e.g. on a membrane or in situ in a tissue section. Visualization and isolation of the hybrids formed is likewise carried out by methods known to those skilled in the art.

According to a preferred feature of the invention, assay sensitivity can be increased by performing the hybridization reaction in the presence of polyethylene glycol. This is believed to operate by a volume exclusion effect which is equivalent to an increase in probe DNA concentration. The molecular weight of the polyethylene glycol is not critical, and material in the range 4000–8000 Daltons has been used with roughly equal effectiveness. The concentration is however quite critical, and is preferably in the range of 1%–8%, particularly 5%–7%, by weight on the volume of the hybridization reaction mixture. For example, when a conventional hybridization reaction mixture is based on 50% by volume of formamide, a 12% wt/vol solution of polyethylene glycol in formamide may be used instead.

The use of polyethylene glycol to increase assay sensitivity in hybridization reactions generally is believed to be novel and constitutes a further aspect of this invention. The technique is applicable to RNA/DNA as well as DNA/DNA hybridization, and is effective when the probe is labelled with a protein such as an enzyme or with another label such as a radioactive isotope.

The invention further provides a probe for carrying out hybridization reactions, which consists of or contains a covalently cross-linked complex formed from a single strand polynucleotide and a positively charged nucleic acid binding detectable protein or polyamine. The probe preferably contains horseradish peroxidase or other enzyme modified with a polyamine as the protein component. A mass ratio of protein to nucleic acid of about 1:5 up to 2:1, particularly about 1:1, is also preferred.

The invention provides a process and a reagent for carrying out hybridization reactions which uses, as a probe, a chemically prepared compound which occurs in high yield (more than 90%), does not require polymerases for its preparation, and makes the separation of precursors and end products superfluous. The preparation time is very short, and the polynucleotides for the probe preparation need not be used in a high purified state. The standard methods for blot hybridization known to those skilled in the art can be used unaltered.

The following features of the invention are believed surprising and advantageous:

(i) that virtually any enzyme (or other detectable protein) can be made into a DNA binding protein by modification with a positively charged protein or polyamine.

(ii) that the presence of enough enzyme in the complex to be readily detectable (for example one molecule of peroxidase for every 5 or so nucleotides) does not significantly affect the hybridization characteristics of the probe. (iii) that the enzymatically-labelled probe survives the rather severe (e.g. 50% formamide, 37° C.) hybridization and washing procedure to leave an active enzyme for subsequent detection.

The following Examples illustrate the invention.

EXAMPLE 1

A) Histone H1 isolation

Histone H1 (21 Kd) was isolated from calf thymus nuclei by perchloric acid extraction, as already described in BBA Vol. 62, pp. 608 to 609, 1962. Lyophilized histone H1 was dissolved in water (5 mg/ml) and stored at $-20°$ C.

B) Biotin labelling

Biotinyl-N-hydroxysuccinimide ester (BHSE) was prepared as described in Methods of Enzymology, Vol. 62, pp. 308 to 315, 1979. 250 mg biotin (Merck), 250 $\mu$Ci ((1.4 $\mu$g) $^3$H-biotin (NEN), 150 mg N-hydroxysuccinimide (Merck) are dissolved in 3 ml dimethyl formamide (DMF) and 200 mg dicyclohexylcarbodiimide are added. The mixture is stirred for 16 hours at 20° C. The precipitate is filtered off and the filtrate is dried in vacuo. The residue is washed with ether, recrystallised from isopropanol, and used thus for the biotin labelling.

Histone H1 was biotinylated to different degrees with increasing amounts of BHSE. 5 $\mu$g BHSE (dissolved in 10 $\mu$l DMF), 25 $\mu$g BHSE (in 10 $\mu$l DMF) and 250 $\mu$g BHSE in 10$\mu$l DMF were added to three solutions containing the same amount of histone H1 (1 mg in 300 $\mu$l of 50 mM NaHCO$_3$) and incubated for 1 hour at 20° C. After dialysis against 5 mM sodium phosphate (pH 6.8) the three samples are stored at $-20°$ C. The concentrations of the biotin-labelled histone H1 solutions are determined by comparison with unmodified histone H1 by SDS-polyacrylamide gel electrophoresis. The number of biotin residues in the three preparations was estimated by the tritium marker contained in BHSE and was found to be between 2.7 and 20 per histone H1 molecule.

C) Polynucleotide-histone H1 complex formation

Circular DNA (plasmids) as well as large linear DNA molecules (phage lambda DNA) were linearised or split with restriction endonucleases to an average size of approximately 4 kb. During the course of the investigation it was found that smaller DNA fragments produce stronger hybridization signals. The DNA was therefore split with enzymes such as Sau 3 A or Hae III. The split DNA was used without further purification. 1 $\mu$g DNA (in not more than 20 $\mu$l splitting buffer) was diluted with 180 $\mu$l freshly prepared 5 mM sodium phosphate buffer (pH 6.8), denatured by heat (100° C., 3 minutes) and cooled for 3 minutes in an ice bath. Histone H1 (between 0.8 and 1.0 $\mu$g in approximately 5 $\mu$l phosphate buffer) was first of all added, followed by 20 $\mu$l of a 2.5% glutaraldehyde solution. The sample was incubated for 10 minutes at 30° C. and added directly to the hybridization vessel containing the nitrocellulose paper and the hybridization solution.

D) Hybridization

The DNA under investigation was split with restriction endonucleases, fractionated by agarose gel electrophoresis, and transferred to nitrocellulose paper by the Southern method (J. Mol. Biol. 98, 503–517, 1975). The papers are soaked for 1 hour at 37° C. in 10× Denhardt's solution (BBA, 23, 641 to 645, 1966), 4× SET (1 × SET=0.15M NaCl, 0.03 M Tris× HCl, pH 8, 1 mM EDTA), and transferred to plastics containers holding between 10 and 20 ml pure hybridization mixture (50% deionised formamide, 2 × Denhardt's solution, 4x SET, 0.1% SDS and 20 $\mu$g/ml yeast T-RNA), incubated for 1 hour at 37° C., and then, after adding the sample, gently shaken for 16 to 20 hours at 37° C.

The nitrocellulose papers were then washed for 60 minutes at 37° C. with two changes of a solution containing 50% formamide, 0.2% SDS and 5× SSC (1 × SSC=0.15M NaCl, 0.015M sodium citrate), and washed for 40 minutes at 20° C. with two changes of solution containing 2× SSC. The filters were dried and developed with a biotin detection system.

E) Visualization of the probes with avidin peroxidase

The nitrocellulose papers were first of all incubated for 20 minutes with a solution containing 10 $\mu$g/ml poly-l-lysine HBr, mol. wt. 220,000 (Sigma), 0.1M Tris HCl (pH 7.5), and then incubated for 50 minutes with a 3% bovine serum albumin (BSA), 0.1M Tris HCl (pH 7.4), and incubated for the next 60 minutes with the avidin peroxidase solution (1M NaCl, 0.1M Tris HCl, pH 7.4, 0.1% Triton X-100, 0.1% BSA and 1 $\mu$g/ml avidin peroxidase, E. Y. Laboratories, Calif.). After 20 minutes' washing with two changes of a solution containing 1M NaCl, 0.1M Tris HCl, pH 7.4, 0.1% BSA and 0.1% Triton X-100, the papers were incubated with the staining solution (10 ml 0.1M Tris HCl, pH 7.4, 2 ml ethanol in which 6 mg of 3,3'-dianisidine had been dissolved, 6 $\mu$l 30% H$_2$O$_2$). The color development (brown bands) occurs within 5 to 10 minutes. All incubation steps were carried out at 20° C. with gentle shaking.

EXAMPLE 2

The same procedure as described in Example 1 was adopted, but instead of a biotin labelling, labelling with $^{125}$I was employed. The labelling of histone H1 was carried out as follows: 60 $\mu$l of a solution containing between 120 and 150 $\mu$g histone H1 and 100 mM sodium borate (pH 8.9) was added at 0° C. to 1 mCi of solid monoiodo $^{125}$I Bolton-Hunter reagent (2000 Ci/mmole) (NEN), and allowed to stand for 1 hour. 10 $\mu$l of 1 glycine in 0.5M sodium borate was then added. The solution was gel filtered through a column treated with 50 $\mu$g histone H1 (silanized Pasteur pipette) (Sephadex G 100 : molecular sieve material based on cross-linked dextran) in 5 mM sodium phosphate, pH 6.8. Fractions containing $^{125}$I-histone H1 were stored at $-20°$ C.

EXAMPLE 3

For gene mapping, a $\lambda$-clone carrying a Drosophila virilis insert was split with various restriction endonucleases, separated according to size, transferred to nitrocellulose paper, and simultaneously hybridized with a reagent according to the invention comprising λ-DNA and $^{125}$I-histone H1 and a reagent according to the invention comprising a plasmid (containing Drosophila virilis sequences of the λ-clone) and biotin-histone H1. Eco R1, Bam H1, Hind III and Sal I were used as restriction endonucleases. The invididual fragments that had been obtained with the various enzymes and which in each case contained the complementary polynucleic acid, where identified by exposure to an x-ray film followed by developing with a biotin detection system. In this way a rapid mapping of the gene was possible.

EXAMPLE 4

20 mg ($5 \times 10^3$ units) of horseradish peroxidase (grade 1, Boehringer Mannheim) was dissolved in 220 µl of 90 mM sodium phosphate, pH 6.0, and 60 µl of a solution containing 30 mg p-benzoquinone in 1 ml ethanol was then added. The mixture was allowed to react for 1 hour at 37° C. in the dark. Peroxidase with covalently bound benzoquinone molecules was separated from unreacted benzoquinone by gel filtration using a 6 ml Sephadex G 100 column in 0.15M NaCl without buffer. The brown-coloured fractions (about 1.8 ml) were combined and the coupling reaction was initiated by increasing the pH value by adding 180 µl of 1M NaHCO$_3$ and adding 2.7 µl (133 µg) of a polyethyleneimine solution (Polymin G 35 BASF). The reaction mixture was kept in the dark for 14 hours at 37° C., and then dialyzed against 5 mM sodium phosphate, pH 6.8, and stored at 3° C. (solution A). The protein concentration of the solution A was approximately 7 µg/µl. No loss of activity was observed during three months' storage.

The size and composition of the peroxidase conjugate was determiend by SDS polyacrylamide gel electrophoresis using $^{125}$I-polyethyleneimine (labelled with Bolton-Hunter reagent) and by comparing Coomassie blue-stained gels with the corresponding autoradiograms. It was found that all perioxidase molecules were present in a modified form. The conjugates have the following sizes and proportion: 50 kDa 10%; 100 kDa 60%; 150 kDa 20%; 200 kDa 5%; 250 kDa 2%. All conjugates exhibited a peroxidase: polyethyleneimine mole ratio of 1.

Preparation of probe

Circular, double strand DNA molecules were linearised with a restriction endonuclease and used without further purification. 1 µg DNA in 20 µl 5 mM sodium phosphate, pH 6.8, was heat denatured (100° C., 3 minutes) and cooled for 3 minutes on ice. 20 µl of solution A was first of all added, followed by 6 µl of a 5% glutaraldehyde solution. The sample was incubated for 10 minutes at 37° C. and was then either added directly to the hybridization reaction, which contained nitrocellulose paper and hybridization solution, or was precipitated by adding 28 µl of a solution containing 40% polyethylene glycol 8000 (Sigma). The mixture was centrifuged for 6 minutes and the precipitate was dissolved in 10 µl 1.5M L-lysine in 5 mM sodium phosphate, pH 6.8, and used for the hybridization. DNA binding investigations with gel filtration columns (Sepharose CL-6B) showed that about 25% of the peroxidase activity was covalently bound to the DNA, which corresponds to a protein: DNA mass ratio of about 30:1. Preferred ratios are in the range 1:1 to 200:1.

Hybridization and visualization of the probes

Nitrocellulose papers (Schleicher & Schull) with immobilized DNA were soaked for 1 hour at 38° C. in 10× Denhardt's solution, 4× SET (1× SET is 0.15M NaCl, 0.03 M Tris-HCl, pH 8, 1 mM EDTA) and 0.1% SDS, and then transferred to a plastics beaker containing between 2 and 20 ml blank hybridization mixture (50% formamide, 2× Denhardt's solution, 4× SET, 0.1% SDS and 30 µg/ml yeast tRNA), incubated at 38° C. for 1 hour while shaking, and then further incubated, after adding the probe, for 2 to 16 hours at 38° C. For the analysis of chicken and human single copy gene sequences, the hybridization was carried out in the presence of polyethylene glycol 8000. The hybridization mixture was modified by using 12% (weight/volume) of polyethylene glycol solution in formamide instead of formamide alone. The nitrocellulose papers were washed for 60 minutes at 38° C. with two changes of a solution containing 50% formamide, 0.4% SDS and 0.5×SSC (1× SSC is 0.15M NaCl, 0.015M sodium citrate) and for 20 minutes at 20° C. with two changes of a solution containing 2× SSC. The filters were then incubated at 20° C. with staining solution in the dark. Peroxidase was visualized with 10 ml of a solution of 100 mM Tris-HCl, pH 7.4, containing 10 mM imidazole, 2 ml ethanol in which 6 mg 3,3'-dianisidine had been dissolved, and 10 µl of 30% H$_2$O$_2$. After the staining the filters were washed and stored in Tris-HCl-imidazole buffer.

EXAMPLE 5

A conjugate of alkaline phosphatase and polyethyleneimine was prepared as described in Example 4. For this purpose 3 mg (350 µl) alkaline phosphatase obtained from calf intestine (Grade 1, Boehringer Mannheim) was dialysed against 0.1 M sodium phosphate, pH 6.0. 90 µl of p-benzoquinone solution, as in Example 4, was added and the mixture was incubated for one hour in the dark at 37° C. After gel chromatography (6 ml column Sephadex G 25) the phosphatase-containing fractions were combined (about 900 µl), and 100 µl 1M NaHCO$_3$ and 20 µg polyethyleneimine were added. The mixture was incubated for 18 hours in the dark at 37° C., dialysed against 5 mM sodium phosphate, pH 6.8, and stored at 3° C. (solution B).

The probe was prepared as described in Example 4, using solution B instead of solution A. The hybridization was also performed as described in Example 4.

The alkaline phosphatase was visualized by adding 15 ml of a solution containing Nitro Blue tetrazolium (NBT) and 5-bromo-4-chloro-3-indoxyl-phosphate-4toluidine salt (BCIP)and prepared as follows: 5 mg NBT was suspended in 5 ml 0.1M Tris-HCl, pH 9.5, 0.1M NaCl, 5mM MgCl$_2$ (buffer A), vigorously stirred for one minute, and briefly centrifuged. The residue was decanted off into 10 ml buffer previously heated to 37° C. 2.5 mg BCIP was then dissolved in 50 µl dimethyl formamide and added drop-wise, while stirring, to the NBT solution. After the color had developed the filters were washed and kept in 100 mM tris-HCl, pH 7.4 containing 5 mM EDTA.

In the accompanying diagram the results of Examples 6 to 14 obtained according to the invention are illustrated in more detail with the aid of the electrophoretograms obtained. In the diagram:

Figure 1:
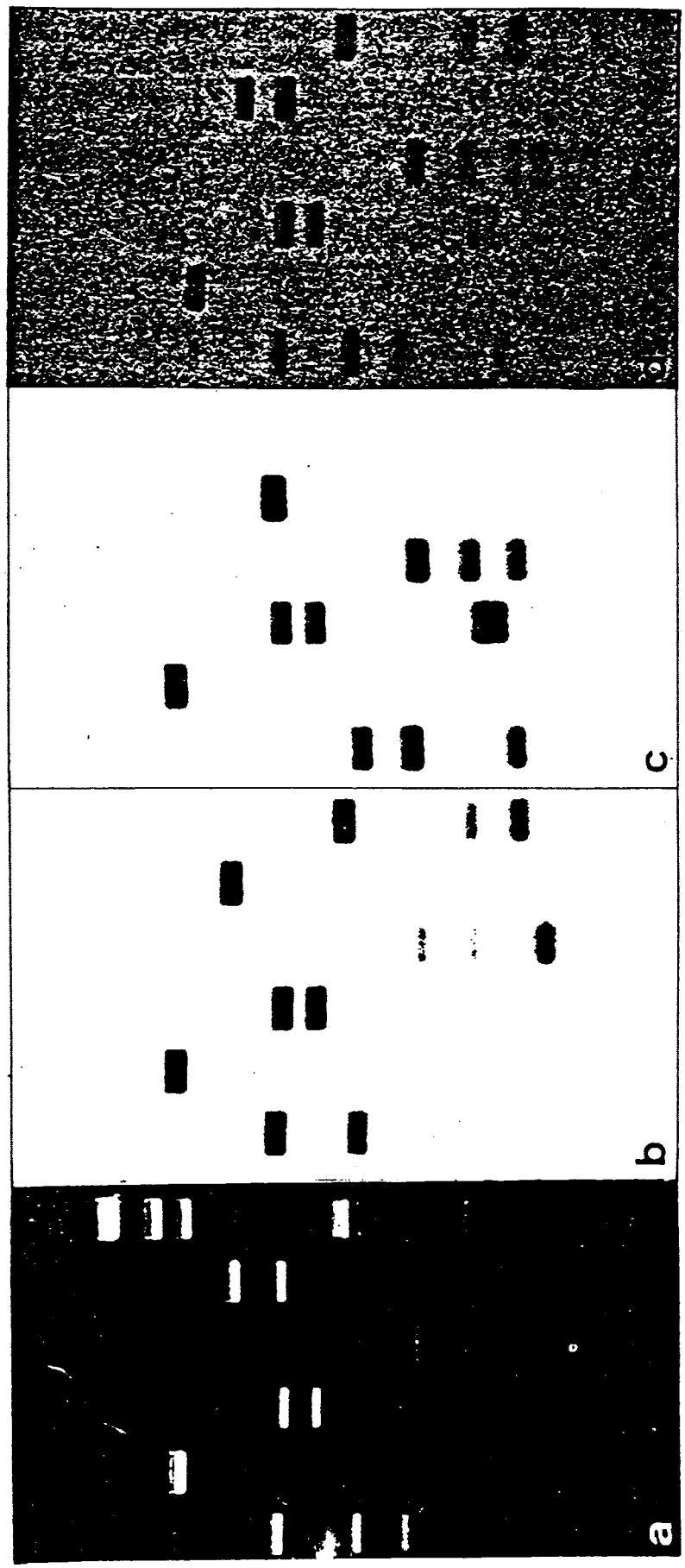
FIG. 1 shows the results of blot hybridization experiments using probes labelled according to the invention.

In FIG. 1 Table a shows an agarose gel electrophoretogram (stained with ethidium bromide) of pHBV 14.1 DNA that had been split with various restriction endonucleases, namely with, from left to right: BamHI, BglII, AvaI, HpaII, PstI. Each spotting track contained 100 ng DNA. The extreme right-hand column contains size markers of the following lengths in kb: 23.1, 9.4, 6.6, 4.4, 2.3, 2.2, 2.0, 1.1, 0.75, 0.56, 0.38 (Example 6).

Table b shows a nitrocellulose paper after transfer of the DNA shown in Table a and hybridization with 0.5 μg of pBR322 DNA split with EcoRI, which was coupled with peroxidase (10 μl of solution A) and stained with anisidine-$H_2O_2$. (Example 7).

Table c shows a replica filter which was hybridized with HBV DNA sequences labelled with peroxidase. The insert (3.2 kb long) of pHBV 14.1 was split with PstI and then subjected to agarose gel electrophoresis and eluted. 0.5 μg of insert DNA thus obtained was labelled with peroxidase (10 μl of solution A). (Example 8).

Table d shows a replica filter that had been hybridized with HBV DNA (labelled with peroxidase) and with pBR322 DNA (labelled with alkaline phosphatase). 0.5 μg of the insert HBV DNA was coupled with peroxidase (10 μg solution A) and 0.5 μg linearized pBR322 DNA was labelled with alkaline phosphatase (10 μl solution B according to Example 5). After the hybridization the filter paper was first of all incubated with the substrate solution for phosphatase, which resulted in a blue coloration, and then with anisidine for visualization of the peroxidase (brown bands). The hybridization volumes and times were respectively 15 ml and 3 hours. (Example 9).

Figure 2:
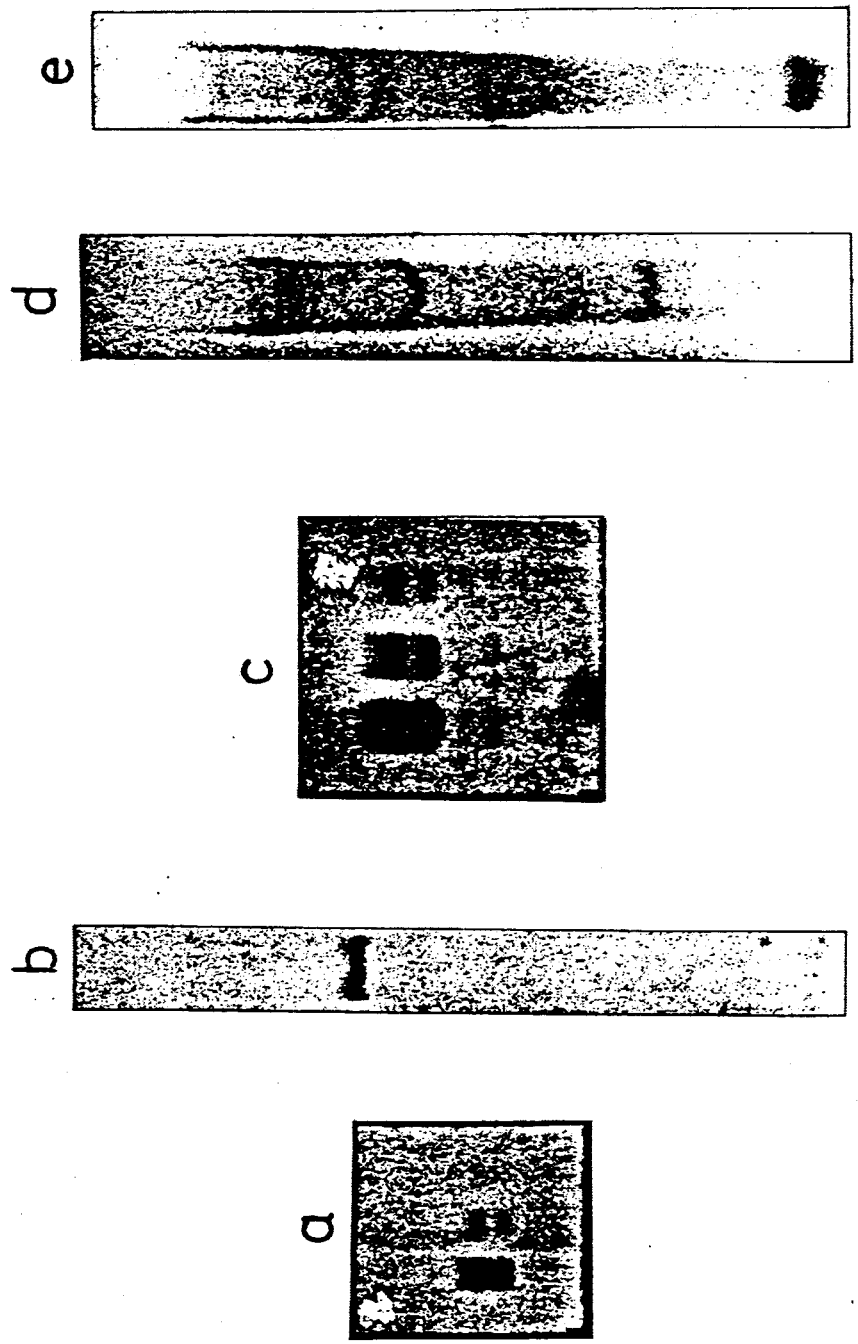
FIG. 2 shows the results of titration and genome blotting experiments.

In FIG. 2 Table a shows the results of the following experiment: pDvl, a pBR322 plasmid which contains a D. virilis insert, was spit with EcoRI and PvuII, four fragments being formed, viz: 2 D. virilis fragments (2.8 and 2.4 kb long) and 2 pBR 322 fragments (2.3 and 2.06 kb long). Serial dilutions (500, 100 and 20 pg per spotting track) were electrophoresed, blotted and hybridized with 0.5 μg of EcoRI linearized pBR322 that had been hybridized with peroxidase (10 μl of solution A) for 16 hours in a volume of 2.0 ml. The two bands in the middle track contain 24 and 21 pg DNA. The fragments in the two bands are 2.3 and 2.06 kb long (Example 10).

Table b) shows a nitrocellulose paper after transfer of 0.75 μg of EcoRI split and electrophoretically separated DNA from D. melanogaster Kc cells, and three hours' hybridization in a volume of 5 ml with 0.5 μg of a EcoRI linearised pBR322 clone with a 4.8 kb insert which carried the alcohol dehydrogenase gene and was coupled to peroxidase (10 μl of solution A). The DNA fragments in the band are 4.8 kb long (Example 11).

Table c) shows the results of a titration experiment similar to a), though in this case the hybridization was carried out in the presence of 6% polyethylene glycol. The two bands in the extreme right-hand row contain 4.7 and 4.1 pg DNA (Example 12).

Table d) shows the results of an experiment in which 10 μg of chicken embryo DNA was split with SacI, subjected to agarose gel electrophoresis, and then transferred to a nitrocellulose filter paper. The hybridization was carried out with 2.5 μg of EcoRI linearized pBR322 plasmid containing 2.5 kb coding sequences for erb A and erb B of chicken erythroblastosis virus that had been coupled to peroxidase (50 μl of solution A). The hybridization time was 14 hours and the volume was 5 ml. They hybridization mixture contained 6% polyethylene glycol. The bands correspond to the following sizes kb: 8.1, 7.5, 5.0, 3.0, 2.5, and 2.1 (Example 13).

Table e) shows the results of an experiment in which 15 μg of human DNA from HeLa cells was split with Hind III, separated according to size by agarose gel electrophoresis and transferred to a nitrocellulose filter paper, and hybridized for 15 hours (in a volume of 5 ml) using 2.5 μg of a EcoRI linearized pKT218 plasmid which contained the coding regions for the albumin gene (2 kb) and was coupled to peroxidase (50 μl solution A). The hybridization mixture contained 6% polyethylene glycol. The bands obtained correspond to the following sizes in kb: 6.2, 4.2, 1.8. (Example 14).

EXAMPLE 6 to 9

To determine whether complexes of single stranded DNA and modified peroxidase were suitable for use as hybridization probes, a pBR322 plasmid containing the genome of hepatitis B virus (HBV) was first digested with different restriction endonucleases, size separated by agarose gel electrophoresis, denatured and chromatographed onto nitrocellulose paper (FIG. 1a). Replicas were hybridized either with pBR322 or HBV DNA both being labelled with peroxidase. After hybridization, the nitrocellulose paper was treated with staining solution (anisidine and $H_2O_2$). Brown colored bands developed after a few minutes. As can be seen in FIGS. 1b and 1c the pattern of bands is different for the two probes used and correspond to that which is expected from pBR322 and hepatitis B genome sequence data.

Using the same approach probes were constructed with another colourimetrically detectable enzyme, namely alkaline phosphatase, and found to have similar hybridization characteristics to peroxidase labelled DNA (not shown). A useful application of this general methodology e.g. for characterization of DNA fragments, exploits the fact that the two different DNA fragments can be labelled with two different enzymes. Another replica blot (FIG. 1a) was hybridized simultaneously with pBR322 DNA (labelled with phosphatase) and HBV DNA (labelled with peroxidase). After hybridization, the nitrocellulose paper was developed first with a substrate for phosphatase leading to blue pigmentation and later with anisidine (FIG. 1d). The differently coloured bands indicate the extent to which complementary sequences to the two probes are present in a given band (compare FIG. 1b and 1c with 1d). These results show that the basic scheme for enzyme labelling of single stranded DNA molecules works.

EXAMPLES 10 to 14

The usefulness of enzyme labelled probes depends by and large on their sensitivity. To determine the limit of detection, reconstruction experiments were performed in which serial dilutions of a double-restricted pBR322 plasmid were first electrophoresed in the prsence of carrier DNA, then blotted and hybridized with peroxidase labelled pBR322 DNA and finally stained. After a 0.5 h incubation in the substrate solution, bands containing 20 pg of DNA of a size of 2 and 2.3 kb respectively could be clearly detected (FIG. 2a). The detection limit of peroxidase labelled probes is therefore slightly less than 20 pg for 2 kb long DNA fragments. The result of this experiment suggests that it should be possible to perform blot analysis of genomes of relatively low complexity. This supposition was tested by digesting DNA from Drosophila melanogaster Kc cells with EcoRI and transferring the resulting fragments to nitrocellulose paper after gel electrophoresis. The DNA was then hybridized for 3 h with a peroxidase labelled alcohol dehydrogenase probe. After a staining time of 20 minutes a band at the expected 4.3 kb position was observed (FIG. 2b). The result of this experiment demonstrates that a single copy gene a few kb long can be visualized after short staining times using an amount of genomic DNA (ca. 1 µg) which workers in Drosophila field generally use.

To detect single copy genes on genomic blots of species with high DNA sequence complexity the sensitivity of peroxidase labelled probes had to be further increased. This was done by adding a neutrally charged synthetic polymer, namely polyethylene glycol (PEG) to the hybridization reaction mixture. A serial dilution experiment similar to the one described above was performed using 6% PEG. After 30 minutes of staining bands containing about 4pg of DNA of about 2 kb length could be clearly detected (FIG. 2c). The limit of detection is therefore in the 1–5 pg range which is sufficient to perform genomic blot analysis of species of high complexity. To test this critically, genomic DNA of chicken and human origin respectively was digested with restriction endonucleases, size separated by electrophoresis, blotted and hybridized in the presence of 6% PEG. The chicken blot was probed with peroxidase labelled erb sequences of avian erythroblastosis virus and the human DNA blot with peroxidase labelled albumin gene sequences. After a 45 minutes incubation with the substrate solution restriction fragments were observed (FIGS. 2d and e) that had sizes in agreement with published values. As an additional control, replica filters were hybridized with nick-translated probes and exposed to X-ray films. The pattern of bands and their intensities on the autoradiograms were indistinguishable if enzyme labelled probes were used (results not shown). These results show that unique avian and mammalian gene sequences can be visualized colourmetrically with peroxidase labelled probes when PEG is used in the hybridization reaction mixture.

I claim:

1. A method of detecting a target single-stranded nucleotide sequence in polynucleotide material by contacting the material under hybridizing conditions with a probe containing a nucleotide sequence complementary to and capable of stable hybridization with the target sequence and thereafter using the probe to detect the target sequence in the material,
   wherein the material is contacted with the probe in the presence of a polyethylene glycol.

2. A method as claimed in claim 1, wherein the polyethylene glycol is present in a concentration of about 6% (w/v).

3. A method as claimed in claim 1, wherein the probe is labelled with an enzyme.

* * * * *